United States Patent
David et al.

[11] 4,040,749
[45] Aug. 9, 1977

[54] ORGANIC VAPOR DETECTION WITH LIQUID CRYSTALS

[75] Inventors: Donald J. David, Centerville; Edgar E. Hardy, Kettering, both of Ohio

[73] Assignee: Monsanto Research Corporation, St. Louis, Mo.

[21] Appl. No.: 705,962

[22] Filed: July 16, 1976

Related U.S. Application Data

[63] Continuation of Ser. No. 547,311, Feb. 5, 1975, abandoned.

[51] Int. Cl.² .................. G01N 21/22; G01N 21/48
[52] U.S. Cl. .................. 356/201; 23/203 LC; 250/227; 350/160 LC; 356/209
[58] Field of Search .......... 356/201, 209; 250/227; 350/160 LC; 23/230 LC, 230 M, 254 R

[56] References Cited

U.S. PATENT DOCUMENTS

| | | | |
|---|---|---|---|
| 3,071,038 | 1/1963 | Vollmer | 250/227 |
| 3,704,060 | 11/1972 | McNaney | 350/160 LC |
| 3,780,307 | 12/1973 | Saeva et al. | 350/160 LC |
| 3,927,977 | 12/1975 | Jacobs | 350/160 LC |

*Primary Examiner*—Vincent P. McGraw
*Attorney, Agent, or Firm*—L. Bruce Stevens

[57] ABSTRACT

A device for detecting organic vapors comprising (a) an elongated waveguide having on the surface thereof a sufficient amount of liquid crystal material sensitive to organic vapor to measurably change the light transmitting capability of said waveguide upon contacting said waveguide with said vapor, (b) a light source positioned to transmit light lengthwise through said waveguide, and (c) means for measuring the light exiting from said waveguide. The device is useful in a method for measuring organic vapors comprising the steps of (a) exposing said waveguide to a gas which may contain organic vapor to which said liquid crystals are sensitive, and (b) transmitting light through said waveguide, and (c) detecting the light transmitted in step (b) as a measure of said organic vapor. Waveguides of the device are separately claimed as a subcombination.

4 Claims, 3 Drawing Figures

ORGANIC VAPOR DETECTION WITH LIQUID CRYSTALS

This is a continuation, of application Ser. No. 547,311 filed Feb. 5, 1975, now abandoned.

CROSS-REFERENCE TO RELATED APPLICATIONS

A patent application Ser. No. 522,558 was filed on Nov. 11, 1974 now abandoned, on an Optical Analytical Device, Waveguide and Method. A patent application Ser. No. 547,312 now abandoned was filed of even date on "Temperature Measurement."

BACKGROUND OF THE INVENTION

1. Field of the Invention

The invention relates to an optical device for detecting organic vapor and method of using the device.

2. Description of the Prior Art

"Liquid Crystals" is an article in Aerospace Medicine, January 1969, pages 35-39 by Toliver, Roach, Roundy and Hoffman. It particularly describes liquid crystals which change color upon being exposed to organic vapors.

Also a technical bulletin by EM Chemicals on "Liquid Crystals" describes on page 7 the use of liquid crystals in gas analysis for such vapors as acetone, benzene, chloroform, petroleum ether, etc., at levels of the order of 1 ppm.

U.S. Pat. No. 3,050,982 describes a "Dew Point Measuring Apparatus" in which moisture deposited on an elongated waveguide changes the light transmitting capability of the waveguide as an indication of dewpoint. Liquid crystals are not involved.

U.S. Pat. No. 3,409,404 describes "Analytical Methods and Devices Employing Cholesteric Liquid Crystalline Materials" and relates to the detection and analysis of matter, for example, gases on a qualitative or quantitative basis. It is stated that reversible effects on liquid crystal optical properties have been observed with common organic solvents, amines, simple alcohols and organic acids . . . etc.

U.S. Pat. No. 3,704,060 describes "Electrically Controllable Light Conducting Device" and the cladding material on the waveguide can be a liquid crystal coating.

U.S. Pat. No. 3,802,760 describes "Devices for Varying Thin Film Waveguide Properties" by a "liquid crystal member" overlaying a portion of the waveguide.

SUMMARY OF THE INVENTION

A device for detecting organic vapors comprising (a) an elongated waveguide having on the surface thereof a sufficient amount of liquid crystal material sensitive to organic vapor to measurably change the light transmitting capability of said waveguide upon contacting said waveguide with said vapor, (b) a light source positioned to transmit light lengthwise through said waveguide, and (c) means for measuring the light exiting from said waveguide. The device is useful in a method for measuring organic vapors comprising the steps of (a) exposing said waveguide to a gas which may contain organic vapor to which said liquid crystals are sensitive, and (b) transmitting light through said waveguide, and (c) detecting the light transmitted in step (b) as a measure of said organic vapor. Waveguides of the device are separately claimed as a subcombination.

The waveguide can be coated with, impregnated with or in some instances can contain a cavity in the waveguide containing the liquid crystal material sensitive to organic vapor material provided the waveguide with added liquid crystal material will adequately transmit light, and in some instance the liquid crystal material may constitute reactive groups attached to the waveguide.

In the case of a coated waveguide, the waveguide might be either solid or hollow, e.g., a hollow or solid cylinder, and in the case of a hollow cylinder the coating could be on the inner or outer surfaces or both, but normally the ends of the solid rods will not be coated rather only the circumferential area except in some cases where it may be desirable to pass the light through a coating on the ends to absorb certain wavelength light. Obviously, the amount of the liquid crystal material on the waveguide needs to be sufficient to give a measurable change of light transmission over the concentration range of organic vapor which the waveguide is designed to detect.

Waveguides can be made from transparent material such as sapphire, glass, Pyrex or other transparent inorganic material; or from transparent plastics such as polystyrene, poly-α-methylstyrene, polymethylmethacrylate or other transparent plastic material. The waveguides can be of any convenient shape and size but for greatest sensitivity will normally be elongated in the direction of the flow of light. Cylindrical waveguides, sometimes called optical fibers, will normally be used, however, square, rectangular, oval or other cross-section fibers or rods can be used.

The first article under prior art from Aerospace Medicine reports various crystals and their utility for detecting organic vapors. Mixtures of liquid crystals, cholesteryl chloride and 60/40 oleyl cholesteryl carbonate and cholesteryl nanonate, were used to detect chloroform, benzene and cyclohexane. Also a mixture of liquid crystals, cholesteryl butyrate, nanonate and erucate, were used to detect the same organic vapors.

The light source can be a commercially available light source being a substantially white light source or can be colored or substantially monochromatic in the infrared, ultraviolet, yellow, orange, green, blue or other color ranges; however, filters can be used to obtain colored light. Monochromatic light in various colors can be supplied by light emitting diodes (LED's). A particular color such as green can be the most desirable depending on the color or composition of the coating developed on the waveguide.

DESCRIPTION OF THE PREFERRED EMBODIMENTS

The waveguide-coated combination can be chosen to provide a coating whose refractive index is either higher or lower than that of the waveguide. The lower refractive index condition is that normally employed in optical guide applications and would result in the mechanism illustrated in FIG. 1A.

Figure 1:
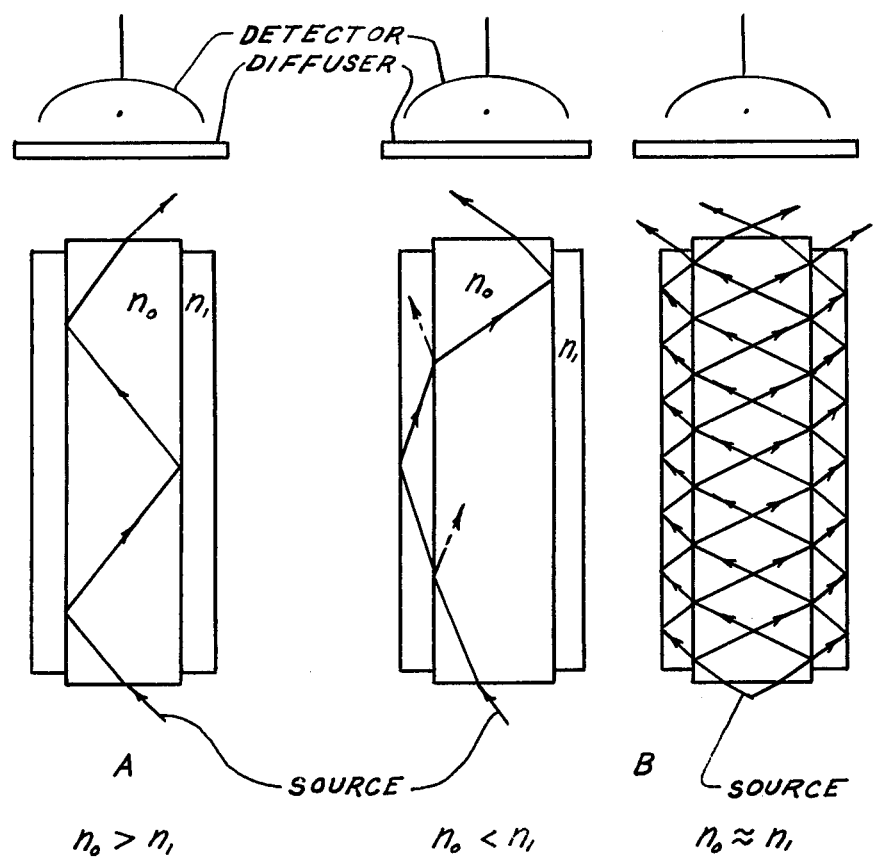
FIG. 1 shows schematic models of light transmitting mechanisms of waveguides of the invention.

Employing the higher refractive index coating, the mechanisms shown in FIG. 1B would be operative. Although either approach can be used, Model 1A would result in lower sensitivity since the evanescent wave interactions occur only in the region of the rod-coating interface. In either of the mechanisms of Model 1B, the radiation is transmitted through the entire coating and in this way allows solid state spectrophotometric measurements to be made in situ.

Figure 2:
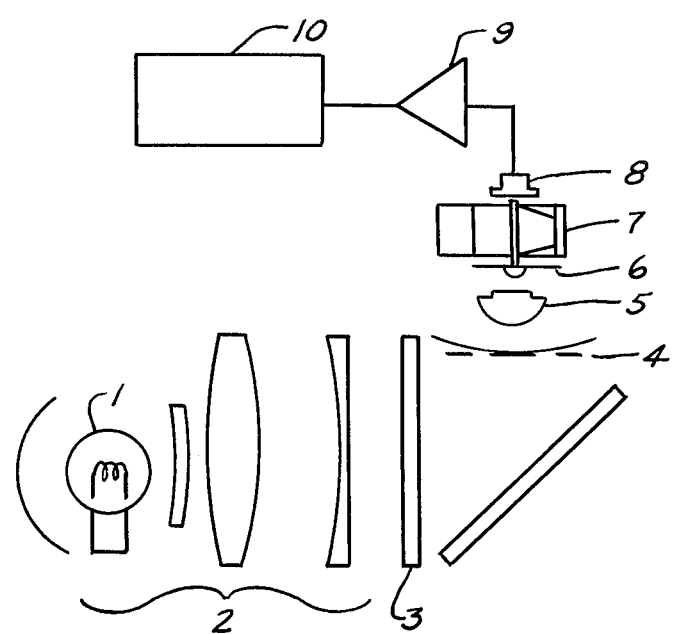
FIG. 2 is a block diagram of a device of the invention.

In order to measure the light transmittance, an instrument or device was designed and constructed to provide quantitative analytical measurements. This particular device accommodates glass rods 0.9 mm to 1.3 mm in diameter and either 10 mm or 20 mm long. A schematic diagram showing the basic components is presented in FIG. 2. The components are:

1. A tungsten filament lamp light source.
2. A condenser system to produce nearly collimated light.
3. A filter for wavelength selection.
4. An annular aperture to block axial light rays.
5. A condenser to produce a hollow cone of light rays.
6. Coupling hemispheres and aperture to couple large angle rays into the rod.
7. A rod mount to accurately position rods with respect to the aperture while presenting a minimum of surface contact.
8. A silicon photodiode detector.
9. An operational amplifier operating as "current-to-voltage" converter.
10. A 3½ digit digital voltmeter for relative transmittance readout.

Figure 3:
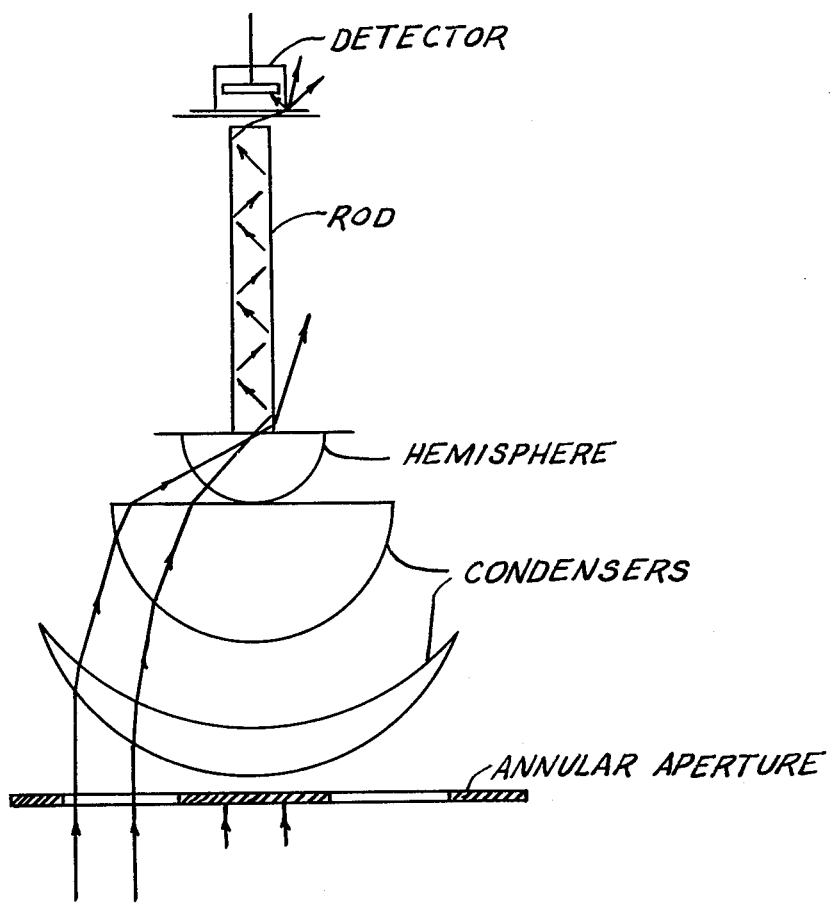
FIG. 3 is a schematic detailed view of the optics of the invention.

A schematic optical diagram is shown in FIG. 3, with rod dimensions exaggerated to show basic instrumental operation. The light from the tungsten lamp is collimated using both mirror and lens condensers. The light then passes through a heat absorbing glass filter and a variable color selection filter. A front surface mirror deflects the light 90° in the vertical direction. An annular aperture blocks axial light rays and defines the range of cone angles for light rays propagating in the quartz rods. The substage condenser converts the collimated beam into a strongly converging hollow cone of light. The hemispherical lens and circular aperture couple the light into the rod.

After multiple reflections within the rod, the light emerges at the upper face and is scattered by a diffuser, part of the light going into the silicon photodiode detector. The photodiode is operated in photovoltaic mode, the operational amplifier acting as a current sink to minimize the voltage across the diode. The amplifier output is a low impedance voltage proportional to the input current over a range of $10^{-11}$ ampere to $10^{-3}$ ampere. An output voltage suitable for the 200 MV full-scale digital panel meter is selected by a decade range switch.

In use, the amount of light transmitted through the rod after coating but before exposure is first recorded with the device. When the coating is exposed to an organic vapor of analytical interest, physical changes occur in the coating, and the transmission of light through the waveguide changes in proportion to the concentration of the organic vapor.

This phenomenon is controlled by the well-known waveguide theories that have been described by Kapany*. The essential factor is that the critical angle beyond which entering light rays are no longer transmitted through the rod is given by $\theta_c = n_i/n_o$, wherein $n_0$, the refractive index of the core, is greater than $n_1$, the refractive index of the coating. Thus, the coated waveguide acts as a sensitive light amplifier whose electrical analog is that of a vacuum tube or transistor-operated amplifier in that a small change on the outer surface of the rod controls a large change in the light transmitted through the rod.

*Kapany, N.S., "Fiber Optics", Academic Press, New York, 1967.

The composition of the liquid crystal material coated on or incorporated into a waveguide is changed to detect different organic vapors and/or varying amounts of organic vapors. Thus having a series of waveguides with coatings sensitive to different organic vapors or amounts of organic vapors allows a waveguide to be selected for use in the device of the invention covering the desired vapor or amount to be detected within the limitations of liquid crystal materials available or which can be made. In most cases the liquid crystal material on the waveguide will go through color changes upon being exposed to the organic vapor and high sensitivities will be provided by the color changes; however, the device of the invention will measure any optical changes affecting light transmission and resulting from changes in liquid crystal material physical changes upon contact with organic vapors sensing changes in refractive index, absorption and/or scattering. The light detection portion of the apparatus can of course be modified to detect color change itself with organic vapor contact. When vapor is removed from contact with waveguide the color changes back to original color which may have been colorless before vapor contact.

Frequently, it is desirable to measure the concentration of organic vapors present in the atmosphere. This is particularly true in those instances where there is a question as to whether or not the safe limits set by OSHA are being exceeded.

Presently, there are a number of methods that can be used, such as gas chromatography, infrared, etc. However, all of these techniques require complex, expensive instrumentation for real time monitoring. Alternate methods involve trapping the vapors in a substance such as activated charcoal, transferring to the laboratory the container with the trapped vapors, and subsequent analysis by appropriate methods. While this technique is simpler and less costly to gather the vapors, it provides only a time average value and not real time analysis.

We have found that it is possible to detect the presence of organic vapors in air by utilizing a waveguide coated with a liquid crystal mixture. This invention covers the use of optical waveguides that are coated with liquid crystals and/or mixtures that are sensitive to organic vapors.

The principle of the technique is as follows: A cholesteric material and/or a mixture of cholesteric materials that are colored at the desired operating temperature are applied to a glass rod of optical quality that functions as a waveguide. The quantity of light transmitted before exposure to air contaminated with hydrocarbons or other materials is relatively constant so that the signal from a detector such as a photodiode operated in the photo-voltaic mode is also relatively constant. The introduction of air, containing organic vapor, causes the helix coiled cholesteric liquid crystal material to change its light transmission and color characteristics. This causes a change in refractive index which alters the amount of light emerging from the waveguide. Thus, a small amount of organic vapor controls a large change in the light transmitted through the rod.

A number of mixtures of liquid crystals have been found to work for this application with different mixtures producing different colors. One that provided about the best results is a commercial mixture (Licrystal 9183) manufactured by E. Merck of Darmstadt, West Germany is described as a temperature indicator 17/24 Licristal, 10% in 1,1,2-trichlorotrifluoroethane, 17° C red, 21° C green and 24° C blue, which comes in 50 ml standard packages. The waveguides are dipped in the solution of Licristal and the solvent evaporates leaving the coating of the liquid crystal material or the solution can be brushed or sprayed on. Waveguides coated with a thin coating of this mixture were exposed to several different vapors. Cyclopentane did not respond, while methylene chloride and ethanol did.

These latter two vapors were obtained simply by passing air over these two liquids at room temperature. The following results were obtained.

| Methylene Chloride Response at 22.5° C | | | |
|---|---|---|---|
| MV $CH_2Cl_2$ | MV Air | Filter | % Change |
| 74.1 | 68.6 | None | 8.0 |
| 57.2 | 55.7 | Red | 2.7 |
| 109.3 | 75.8 | Orange/Yellow | 40.2 |
| 212.0 | 123.7 | Green | 71.4 |

| Ethanol at 24.0° C | | | |
|---|---|---|---|
| MV $C_2H_5OH$ | MV Air | Filter | % Change |
| 71.0 | 69.5 | None | 0.72 |
| 54.8 | 55.2 | Red | −0.72 |
| 105.4 | 92.3 | Orange/Yellow | 14.2 |
| 212.5 | 139.1 | Green | 60.0 |

The described temperature monitor and indicator has the following advantages:

1. Provides a quick and simple way of monitoring the presence of organic vapors and other materials that cause a color change in the liquid crystal mixtures with which the waveguide is coated.

2. Allows detection of small quantities of materials in a gaseous medium which in itself is unreactive with the coated waveguide.

3. Can be easily used to control an on-off function directly from the signal output.

4. Sensitivity can be adjusted by altering the length of the rod or the angle at which light enters the rod.

5. Can be used as a portable monitor.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

We claim:

1. A device for detecting organic vapors comprising
   a. an elongated waveguide having on the surface thereof a sufficient amount of liquid crystal material sensitive to organic vapor to measurably change the light transmitting capability of said waveguide upon contacting said waveguide with said vapor.
   b. a light source positioned to transmit light lengthwise through said waveguide, and
   c. means for measuring the light exiting from said waveguide.

2. A device of claim 1 wherein said waveguide has a coating of said liquid crystals on the peripheral surface of said waveguide.

3. A method for detecting organic vapor comprising the steps of
   a. exposing a waveguide having on the surface thereof a sufficient amount of liquid crystal material sensitive to organize vapor to measurably change the light transmitting capability of said waveguide upon contacting said waveguide with said vapors to a gas which may contain organic vapor to which said liquid crystals are sensitive,
   b. transmitting light through said waveguide after exposure in step (a), and
   c. detecting the light transmitted in step (b) as a measure of said organic vapor.

4. A method of claim 3 wherein said waveguide has a coating of said liquid crystals on the peripheral surface of said waveguide.

* * * * *